US00PP31988P2

(12) United States Plant Patent
van der Zwet

(10) Patent No.: US PP31,988 P2
(45) Date of Patent: Jul. 14, 2020

(54) ***MONARDA* PLANT NAMED 'JULIETTE'**

(50) Latin Name: ***Monarda* L.**
Varietal Denomination: Juliette

(71) Applicant: Alexius Joannes Joseph van der Zwet, Oude-Wetering (NL)

(72) Inventor: Alexius Joannes Joseph van der Zwet, Oude-Wetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 16/501,553

(22) Filed: Apr. 29, 2019

(51) Int. Cl.
*A01H 5/02* (2018.01)
*A01H 6/50* (2018.01)

(52) U.S. Cl.
USPC ..... Plt./455

(58) Field of Classification Search
USPC ..... Plt./455
CPC ..... A01H 5/02; A01H 6/60
See application file for complete search history.

*Primary Examiner* — Keith O. Robinson
(74) *Attorney, Agent, or Firm* — C. A. Whealy

(57) ABSTRACT

A new and distinct cultivar of *Monarda* plant named 'Juliette', characterized by its upright and tall plant habit; freely branching habit; dark green-colored leaves; freely flowering habit; large inflorescences with light red purple to purple-colored flowers; relatively resistant to Powdery Mildew; and relatively tolerant to low temperatures.

2 Drawing Sheets

Botanical designation: *Monarda* L.
Cultivar denomination: 'JULIETTE'.

BACKGROUND OF THE INVENTION

The present invention relates to a new and distinct cultivar of *Monarda* plant, botanically known as *Monarda* L., typically grown as a cut flower plant and hereinafter referred to by the name 'Juliette'.

The new *Monarda* plant is a product of a planned breeding program conducted by the Inventor in Oude-Wetering, The Netherlands. The objective of the breeding program is to create new upright and freely branching *Monarda* plants with numerous attractive flowers and disease-resistance.

The new *Monarda* plant originated from an open-pollination in 2015 of an unidentified selection of *Monarda* L., not patented, as the female, or seed, parent with an unknown selection of *Monarda* L. as the male, or pollen, parent. The new *Monarda* plant was discovered and selected by the Inventor as a single flowering plant from within the progeny of the stated open-pollination grown in a controlled environment in Oude-Wetering, The Netherlands in 2016.

Asexual reproduction of the new *Monarda* plant by softwood vegetative cuttings in Lisserbroek, The Netherlands, since 2016 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Juliette'.

These characteristics in combination distinguish 'Juliette' as a new and distinct *Monarda* plant:

1. Upright and tall plant habit.
2. Freely branching habit.
3. Dark green-colored leaves.
4. Freely flowering habit.
5. Large inflorescences with light red purple to purple-colored flowers.
6. Relatively resistant to Powdery Mildew.
7. Relatively low temperature tolerant.

Plants of the new *Monarda* differ primarily from plants of the female parent selection in plant height as plants of the new *Monarda* are taller than plants of the female parent selection. In addition, plants of the new *Monarda* are more tolerant to Powdery Mildew than plants of the female parent selection.

Plants of the new *Monarda* can be compared to plants of *Monarda didyma* 'Pink Lace', disclosed in U.S. Plant Pat. No. 18,367. In side-by-side comparisons, plants of the new *Monarda* differ primarily from plants of 'Pink Lace' in the following characteristics:

1. Plants of the new *Monarda* are taller than plants of 'Pink Lace'.
2. Plants of the new *Monarda* have slightly darker red purple-colored flowers than plants of 'Pink Lace'.

Plants of the new *Monarda* can also be compared to plants of *Monarda didyma* 'Squaw', not patented. In side-by-side comparisons, plants of the new *Monarda* differ primarily from plants of 'Squaw' in the following characteristics:

1. Plants of the new *Monarda* flower for a longer period of time than plants of 'Squaw'.
2. Plants of the new *Monarda* have red purple-colored flowers whereas plants of 'Squaw' have red-colored flowers.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical flowering plant of 'Juliette' grown in a container.

The photograph on the second sheet is a close-up view of a typical inflorescence of 'Juliette'.

DETAILED BOTANICAL DESCRIPTION

The aforementioned photographs and following observations, measurements and values describe plants grown during the summer in 17-cm containers in an outdoor nursery in Lisserbroek, The Netherlands and under cultural practices typical of commercial *Monarda* production. During the production of the plants, day temperatures ranged from 18° C. to 30° C. and night temperatures ranged from 6° C. to 18° C. Plants were one year old when the photographs and description were taken. In the detailed description, color references are made to The Royal Horticultural Society Colour Chart, 2015 Edition, except where general terms of ordinary dictionary significance are used.

Botanical classification: *Monarda* L. 'Juliette'.

Parentage:

*Female, or seed, parent*.—Unidentified selection of *Monarda* L., not patented.

*Male, or pollen, parent*.—Unknown selection of *Monarda* L., not patented.

Propagation:

*Type cutting*.—By softwood vegetative cuttings.

*Time to initiate roots, summer*.—About two to three weeks at temperatures about 20° C.

*Time to initiate roots, winter*.—About four weeks at temperatures about 20° C.

*Time to produce a rooted young plant, summer*.—About five weeks at temperatures about 20° C.

*Time to produce a rooted young plant, winter*.—About two months at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; tall and upright plant habit; narrow inverted triangular in overall plant shape; moderately vigorous growth habit; moderate to rapid growth rate.

*Plant height, soil level to top of foliar plane*.—About 65 cm.

*Plant height, soil level to top of floral plane*.—About 68.8 cm.

*Plant width*.—About 37.5 cm.

*Lateral branch description* (*peduncles*).—Branching habit: Freely basal branching habit with potentially about eight main stems developing per plant. Length: About 56.4 cm. Diameter: About 3 mm. Internode length: About 10.9 cm. Strength: Strong. Aspect: Erect to about 30° from vertical. Texture and luster: Sparsely pubescent; slightly glossy. Color: Close to 144A; side exposed to direct sunlight, tinged with close to 182B.

Leaf description:

*Arrangement*.—Opposite, simple.

*Length*.—About 7.1 cm.

*Width*.—About 3.1 cm.

*Shape*.—Ovate.

*Apex*.—Acuminate to long apiculate.

*Base*.—Truncate.

*Margin*.—Serrate.

*Texture and luster, upper surface*.—Densely pubescent; slightly rugose; slightly glossy.

*Texture and luster, lower surface*.—Densely pubescent; moderately rugose; matte.

*Venation pattern*.—Pinnate.

*Color*.—Developing leaves, upper surface: Close to 137B. Developing leaves, lower surface: Close to 138A. Fully expanded leaves, upper surface: Close to NN137A; venation, close to 146B. Fully developed leaves, lower surface: Close to 147B; venation, close to 146D.

*Petioles*.—Length: About 1.4 cm. Diameter: About 1.5 mm. Strength: Strong. Texture and luster, upper surface: Smooth, glabrous; slightly glossy. Texture and luster, lower surface: Sparsely pubescent; matte. Color, upper surface: Close to 146D tinged with close to 184A. Color, lower surface: Close to 145A and 145B.

Flower description:

*Flower form, arrangement and flowering habit*.—Single labiate flowers arranged in large terminal globular spikes; flowers sessile; flowers face upright to outwardly; freely flowering habit with about 150 flowers developing per inflorescence and about 600 flowers per plant at one time.

*Natural flowering season*.—Plants flower for about ten weeks during the summer in The Netherlands; plants begin flowering about three months after planting.

*Postproduction longevity*.—Flowers maintain good substance for about one week on the plant; flowers not persistent.

*Fragrance*.—None detected.

*Flower buds*.—Length: About 2.4 cm. Diameter: About 3 mm. Shape: Narrowly oblanceolate, curved. Texture and luster: Densely pubescent; matte. Color, immature petals: Close to 68B; proximally, close to 68D; distally, close to 71D. Color, immature calyx: Close to 187A; proximally, close to 187D; at the base, close to 145B; distal margin, close to 200A.

*Inflorescence height*.—About 4.7 cm.

*Inflorescence diameter*.—About 5 cm.

*Flower diameter*.—About 5.5 mm.

*Flower length*.—About 1.5 cm.

*Flower depth* (*height*).—About 3.3 cm.

*Flower throat diameter*.—About 2 mm.

*Flower tube length*.—About 2 cm.

*Petals*.—Arrangement: Labiate; upper lip hooded; lower lip, a single lobe; 60% of lips fused proximally. Length, upper and lower lips: About 3.3 cm. Width, upper lip: About 1.5 mm. Width, lower lip: About 5.5 mm. Shape, upper lip: Lanceolate; apex, narrowly acute. Shape, lower lip: Oblanceolate; apex, broadly caudate. Margin, upper lip: Entire; not undulate. Margin, lower lip: Entire; moderately undulate. Texture and luster, upper and lower lips, upper surface: Smooth, glabrous; slightly velvety; matte. Texture and luster, upper and lower lips, lower surface: Densely pubescent; slightly velvety; matte. Texture and luster, throat: Smooth, glabrous; matte. Texture and luster, tube: Densely pubescent; matte. Color, upper lip: When opening, upper and lower surfaces: Close to 68B. Fully opened, upper and lower surfaces: Close to 68B; venation, close to 68B; color does not change with development. Color, lower lip: When opening, upper surface: Close to 69C to 69D; margins, close to 68B to 68D. When opening, lower surface: Close to 68B to 68C. Fully opened, upper and lower surfaces: Close to 75B to 75C; venation, close to 75B to 75C; color does not change with development. Color, throat: Close to 68B; venation, close to 68B. Color, tube: Close to 68B; towards the base, close to NN155D; venation, close to 68B and NN155D.

*Sepals*.—Quantity and arrangement: Five in a single whorl; proximally 90% fused into a tubular calyx. Length: About 9 mm. Width: About 0.75 mm. Shape: Narrowly oblong. Apex: Acute. Margin: Free part, entire. Texture and luster, upper surface: Smooth, glabrous; matte. Texture and luster, lower surface: Mostly smooth, glabrous; distally, moderately pubescent; slightly glossy. Color: When opening, upper surface: Close to 186C; proximally, close to 147D; apical margin, close to N186C; venation, close to 186A. When opening, lower surface: Close to 187A; proximally, close to 187D and 145B; apical margin, close to 200A; venation, similar to lamina. Fully opened, upper surface: Close to 186C; proximally, close to 147D; apical margin, close to N186C; venation, close to 186A. Fully opened, lower surface: Close to N187D; proximally, close to 147D; apical margin, close to between N186C and 200A; venation, similar to lamina.

*Floral bracts*.—Quantity and arrangement: About 20 subtending the inflorescence. Length: About 1.8 cm. Width: About 7 mm. Shape: Ovate to lanceolate. Texture, upper surface: Smooth, glabrous; slightly velvety. Texture, lower surface: Moderately pubescent. Color, upper surface: Close to N77A and N77B; towards the margins, tinged with close to 146B. Color, lower surface: Close to 144B; towards the margins, close to 146A; slightly tinged with close to 187B.

*Peduncles* (*see lateral branch description*).—

*Reproductive organs*.—Stamens: Quantity per flower: Two. Filament length: About 1.2 cm. Filament color: Close to NN155D. Anther size: About 2 mm by 0.75 mm. Anther shape: Narrowly elliptical; dorsifixed. Anther color: Close to 68A and 68B. Pollen amount: Scarce. Pollen color: Close to NN155A. Pistils: Quantity per flower: One. Pistil length: About 3.2 cm. Stigma diameter: About 1 mm. Stigma shape: Cleft, unequal. Stigma color: Close to 70A to 70B. Style length: About 3 cm. Style color: Close to 70B; proximally, close to NN155D. Ovary color: Close to 153D.

*Seed and fruit*.—To date, seed and fruit production have not been observed on plants of the new *Monarda*.

Pathogen & pest resistance: Plants of the new *Monarda* have been observed to be relatively resistant to Powdery Mildew (*Erysiphe cichoracearum*). Plants of the new *Monarda* not been observed to be resistant to pests and other pathogens common to *Monarda* plants.

Garden performance: Plants of the new *Monarda* have exhibited good tolerance to rain, wind and temperatures ranging from about −29° C. to 40° C. and to be suitable for USDA Hardiness Zones 5 to 10.

It is claimed:

1. A new and distinct *Monarda* plant named 'Juliette' as illustrated and described.

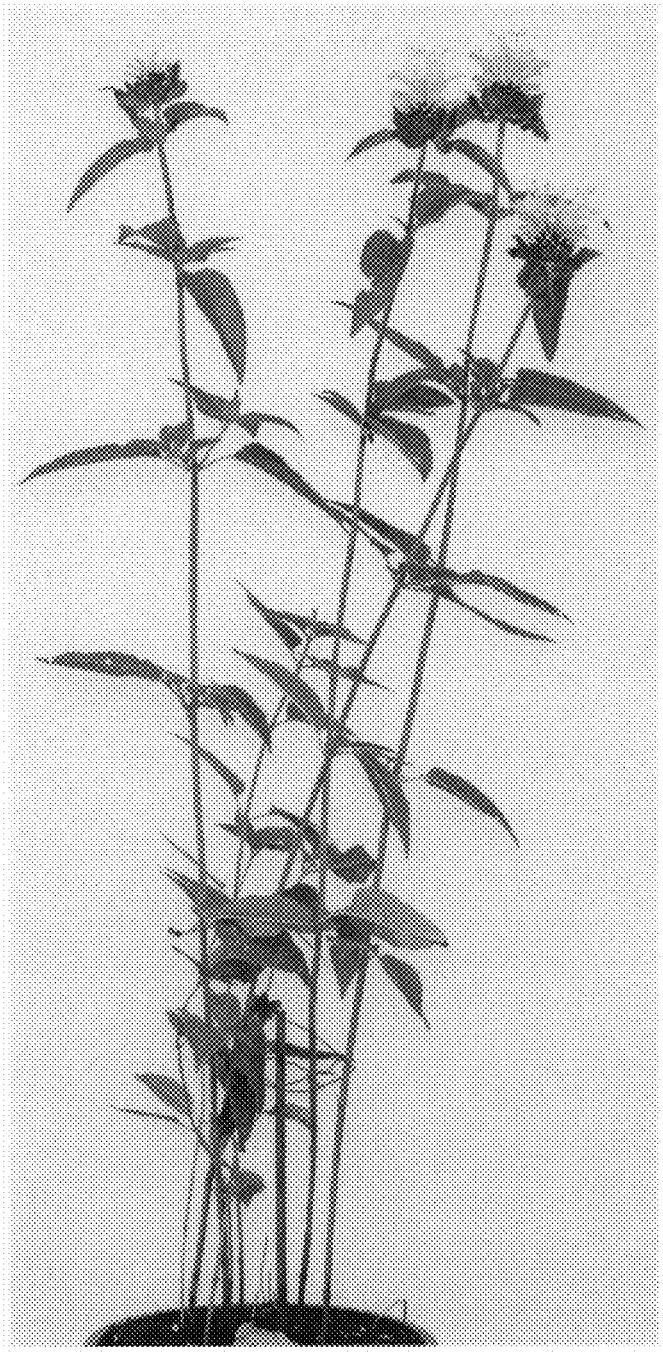

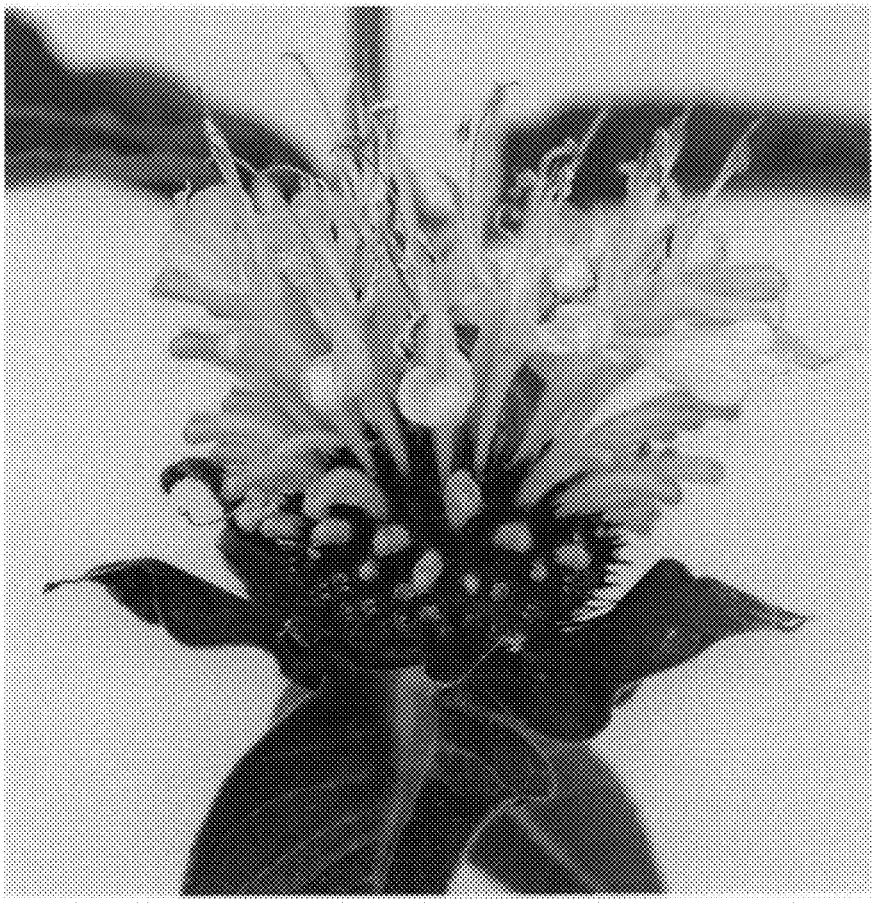

* * * * *